(12) United States Patent
Schmuck et al.

(10) Patent No.: US 6,255,093 B1
(45) Date of Patent: Jul. 3, 2001

(54) RECOMBINANT MICROBIAL 3-HYDROXYBUTYRATE DEHYDROGENASE A PROCESS FOR ITS PRODUCTION AND THE USE THEREOF

(75) Inventors: Rainer Schmuck, Benediktbeuern; Rainer Müller, Penzberg; Harald Weisser, Bernried; Alfred Engel, Penzberg; Kerstin Krüger, München, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/287,097

(22) Filed: Apr. 7, 1999

(30) Foreign Application Priority Data

Apr. 8, 1998 (DE) .............................. 198 15 685

(51) Int. Cl.[7] ................ C12N 9/04; C07K 1/00
(52) U.S. Cl. ............................ 435/190; 530/350
(58) Field of Search ................ 435/190; 530/350

(56) References Cited

PUBLICATIONS

Anega et al., J. Bacteriology, 181(3), 849–857, Feb. 1999.*

* cited by examiner

*Primary Examiner*—Rebecca E. Prouty
*Assistant Examiner*—M. Monshipouri
(74) *Attorney, Agent, or Firm*—Arent Fox Plotkin Kintner Kahn Pllc.

(57) ABSTRACT

DNA molecule comprising a structural gene which codes for a bacterial protein with the enzymatic activity of 3-hydroxybutyrate dehydrogenase (3-HBDH), a recombinant DNA containing the DNA molecule, microorganisms transformed accordingly, a process for obtaining 3-HBDH by culturing a suitable transformed microorganism as well as a method for the determination of ketone bodies in the presence of the enzyme. A structural gene from Rhodobacter sphaeroides is preferred.

7 Claims, 4 Drawing Sheets

Figure 1

```
   1    ccgcccttcg gcgcgtcggg atttgcatat ggcagagaca caaaatccgg
  51    tggaagcgcc ggttcgccat acatagctat gccgtgccgg ggttcggcgg
 101    ccagcgtcgt gcccagaacg gcaagcccga gagccagcgc ggcgccctc
 151    aggcgggacc ggaattcctg tatcattcgg gcaacagctc ctcggtggcc
 201    gatccgcagg gggccagatt tacccgcggg cggtaacctt ttcaaacttt
 251    taccttggac agcggcggag aaggtcgtat aagtatccca ctgctcgata
 301    ggtttcttgc ctgtatgaaa cctgcctcaa cgacttaacg ccggcttcgc
 351    gccggcgttt ttttttcgcgc ttcgcgaatg acaggcgccc cggtctccgt
 401    gccatctcgc catcccgcgg cccattggct aggtcttggc cagtgcacat
 451    gacgggaggc aggatcATGG ATCTGAACGG CAAGCGGGCA ATCGTCACCG
 501    GCTCGAACTC GGGCATCGGG CTGGCTGCG CCGAAGAGCT GGCGCGCGCC
 551    GGCGCCGAGG TTGTCATCAA CTCCTTCACC GACCGCGACG AGGATCACGC
 601    GCTGGCCGAG AAGATCGGCC GCGAACATGG CGTGAGCTGC CGCTACATCG
 651    CGGCCGACAT GTCGGACGGC GAAGCGTGCC GGGCGCTGAT CGAGACGGCG
 701    GGCGGCTGCG ACATCCTCGT GAACAACGCG GGCATCCAGC ATGTCTCGTC
 751    GATCGAGGAG TTCCCGGTCG GGAAGTGGAA CGCGATCCTC GCGATCAACC
 801    TCTCGTCGGC CTTCCACACC ACGGCGGCGG CGCTGCCGGG GATGCGGGCG
 851    AAGGGCTGGG GCGGATCGT CAACATCGCC TCGGCGCACG GCTGACGGC
 901    GAGCCCCTAC AAGTCGGCCT ATGTCGCGGC CAAGCACGGG GTGGTGGGCT
 951    TCACCAAGGT CACCGCGCTC GAGACCGCGG GCAAGGGCAT CACCTGCAAC
1001    GCGATCTGCC CGGGCTATGT GCTGACGCCG CTGGTCGAGG CGCAGATCCC
1051    CGACCAGATG AAGGCGCACG ACATGGACCG CGAGACGGTG ATCCGCGAGG
1101    TGATGCTCGA CCGCCAGCCC TCGCGCCAGT TCGCAACGAC CGGTCAGATC
1151    GGCGGCACGG TGGTGTTCCT CTGCTCGGGT GCGGCCGATC AGATCACCGG
1201    GACGACGATC TCGGTGGATG GGGCTGGAC CGCCCTCtga cgggcggtcc
1251    ttcggcaact cccgggtcag cctctggcga tggcgcgggc gatgtcggtc
1301    gcgagccggg cgttcgacag gacgagcgcc cggttggcct cgagcgaccg
1351    gccctcggtc agatcgaaga tcaggtcgag caggaacggc gtcacggcct
1401    tggcgg
```

Figure 2

```
  1    MDLNGKRAIV TGSNSGIGLG CAEELARAGA EVVINSFTDR DEDHALAEKI
 51    GREHGVSCRY IAADMSDGEA CRALIETAGG CDILVNNAGI QHVSSIEEFP
101    VGKWNAILAI NLSSAFHTTA AALPGMRAKG WGRIVNIASA HGLTASPYKS
151    AYVAAKHGVV GFTKVTALET AGKGITCNAI CPGYVLTPLV EAQIPDQMKA
201    HDMDRETVIR EVMLDRQPSR QFATTGQIGG TVVFLCSGAA DQITGTTISV
251    DGGWTAL
```

RECOMBINANT MICROBIAL 3-HYDROXYBUTYRATE DEHYDROGENASE A PROCESS FOR ITS PRODUCTION AND THE USE THEREOF

The invention essentially concerns a DNA molecule which codes for a protein with the enzymatic activity of 3-hydroxybutyrate dehydrogenase (E.C.1.1.1.30), recombinant DNA containing the DNA molecule, correspondingly transformed microorganisms, a process for isolating 3-hydroxybutyrate dehydrogenase by culturing a suitable transformed microorganism as well as a method for determining ketone bodies in the presence of the enzyme.

3-Hydroxybutyrate dehydrogenase (3-HBDH) is an enzyme which catalyses the oxidation of hydroxybutyric acid to acetoacetic acid while simultaneously converting $NAD^+$ into NADH (Bergmeyer, H. U. et al. (1967), Biochem. J. vol. 102, 423–431):

The enzyme is used to detect ketone bodies. Ketone bodies are understood in particular as acetoacetic acid, 3-hydroxybutyric acid and acetone. The formation of ketone bodies is increased when lipolysis is increased e.g. in insulin deficiency (diabetes mellitus; type I diabetics), when the glucagon concentration is increased and in a fasting state. In such cases the physiological concentration of less than 7 mg/dl can increase to more than 10-fold. Over the past years hydroxybutyric acid has proven to be an extremely reliable parameter for monitoring an insulin therapy.

Ketone bodies are metabolites of fat metabolism. They are formed in the liver and are subsequently metabolized especially in the musculature. Ketone bodies are usually detected qualitatively by an interference-prone test for acetone or acetoacetic acid. However, in comparison to acetone or acetoacetic acid, 3-hydroxybutyric acid (3-HB) is a more dominant and reliable indicator for clinical diagnoses. The ratio of 3-HB to acetone or acetoacetic acid is normally 3:1. In keto-acidoses the ratio increases to 6:1 to 12:1. Furthermore a suitable 3-HBDH should enable the development of a quantitative test for 3-hydroxybutyric acid.

It is known that 3-HBDH occurs in a number of eukaryotic organisms as well as in prokaryotes (Churchill, P. et al. (1992), Biochem. vol. 31, 3793–3799; Marks, A. R. et al. (1992), J. Biol. Chem. vol. 267, 15459–15463; Bergmeyer, H. U. et al. (1967), Biochem. J. vol. 102, 423–431). Nowadays various bacteria serve in particular as a source for the isolation of the 3-HBDH enzyme. However, the classical processes for producing the conventional 3-HBDH from certain microorganisms are very time-consuming and costly, which is due, on the one hand, to the weak expression of 3-HBDH and, on the other hand, the fermentation process for suitable microorganisms is poorly reproducible.

Hence the object of the present invention is to provide a recombinant microbial protein with the enzymatic activity of 3-HBDH.

The object is achieved by a DNA molecule comprising a structural gene which codes for a protein with the enzymatic activity of 3-hydroxybutyrate dehydrogenase and is transformed and expressed in a heterologous microorganism by means of a vector.

The DNA molecule or the 3-HBDH structural gene according to the invention is in particular the gene coding for 3-HBDH which can be obtained from various microorganisms such as for example from bacteria of the genera Rhodobacter, Rhodospirillum and Pseudomonas. Species of microorganisms from the genus Rhodospirillaceae, in particular *Rhodobacter sphaeroides*, have proven to be particularly suitable as a source of the DNA molecule according to the invention. In particular a gene coding for 3-HBDH was obtained from *Rhodobacter sphaeroides* (BMTU 109, DSM 12077) which has a nucleotide sequence according to SEQ ID NO.1 or a degenerate sequence based on the genetic code. The Rhodobacter 3-HBDH structural gene has a homology to corresponding eukaryotic genes of only 46 or 47% and is also characterized by a GC content of ca 68 mol % and the codon TCG preferably coding for the amino acid serine (12 out of a total of 15) and CTG/C coding exclusively for the amino acid leucine (a total of 16). The strain *Rhodobacter sphaeroides* with the internal name BMTU 109 was deposited on the 26.03.1998 at the "Deutsche Sammlung von Mikroorganismen und Zellkulturen GmbH (DSM)", Mascheroder Weg 1b, D-38124 Braunschweig under DSM 12077.

According to the invention it is also preferred that the 3-HBDH protein is expressed by using a partial sequence contained in SEQ ID NO.1 which is inserted into a suitable vector. Those DNA molecules have proven to be particularly suitable according to the invention which correspond to a nucleotide sequence from nucleotide number 467 to number 1237 of the sequence according to SEQ ID NO.1, which are complementary to this and/or hybridize with this. Such DNA molecules include for example fragments, modifications, derivatives and all variants of the DNA molecules described above. In this connection the term "hybridization" means a hybridization under conventional hybridization conditions, preferably under stringent conditions.

Examples of stringent conditions suitable for use in accordance with the invention can be found in Sambrook et al., 1989, Molecular Cloning: A Laboratory Manual, 2nd Ed., Cold Spring Harbor Laboratory, New York, which is hereby incorporated by reference. See specifically sections 1.101–1.104 and 9.47–9.55, which provide conditions well known to those of skill in the art. For example, suitable stringent conditions include washing for one hour in the presence of 1×SSC and 0.1% SDS at 55° C., preferably at 62° C. A further preferred method is using 0.2×SSC and 0.1% SDS at 55° C. The hybridization conditions mentioned in this reference are in general suitable in order to determine DNA molecules which are complementary to and/or hybridize with the nucleic acid sequences in accordance with the invention.

It should additionally be emphasized that in principle several parameters must be considered when calculating the optimal stringent hybridization conditions including, e.g., the probe length, probe concentration, pH value, temperature, and the presence of monovalent cations and/or formamide.

The following specific stringent hybridization conditions have been successfully applied in the present invention: 50% formamide, 5×SSC, 2% blocking reagent (for decrease of background; Roche Molecular Biochemicals, Cat. No. 1 096 176), 1% lauroylsarcosin and 0.02% SDS at 42° C., with a hybridization time of 1–16 hours.

A further subject matter of the invention is a process for the production of a protein with 3-HBDH activity by inserting a DNA molecule coding for 3-HBDH into a suitable vector and transforming the recombinant DNA obtained into a microorganism which is able to produce 3-HBDH in the medium. Suitable microorganisms for the expression are in particular those of the genus *E. coli* such as for example HB101 (ATCC 33694), JM83 (ATCC 35607) and RR1 (ATCC 35102).

According to the invention all plasmid vectors have proven to be suitable for such a process which are usually used for expression in host cells. Vectors based on the plasmid pKK177 under the control of a T5 promoter are mentioned here as an example. After fermentation of the transformed host cells for several hours, the accumulated protein with the enzymatic activity of 3-HBDH is isolated from the culture medium. The enzyme is essentially isolated by methods known to a person skilled in the art such as by centrifugation, lysis of the biomass, resuspension in a suitable buffer solution, separation of insoluble cell components and by various chromatographic steps for example by means of hydrophobic column materials (e.g. phenyl Sepharose) or/and suitable affinity chromatography.

The recombinant 3-HBDH enzyme can be obtained from the heterologous microorganism in good yields with a purity of ca. 60% to 80% and with a specific activity of at least 200 U/mg. The recombinant bacterial enzyme according to the invention is shortened at the C-terminal end compared to the known eukaryotic 3-HBDH enzymes by preferably ca. 30 amino acids and additionally has no phosphatidylcholine dependency. An advantage of the latter is that it is not necessary to add external lipid (phosphatidylcholine) to develop the enzymatic activity i.e. for example when determining ketone bodies.

Figure 2:
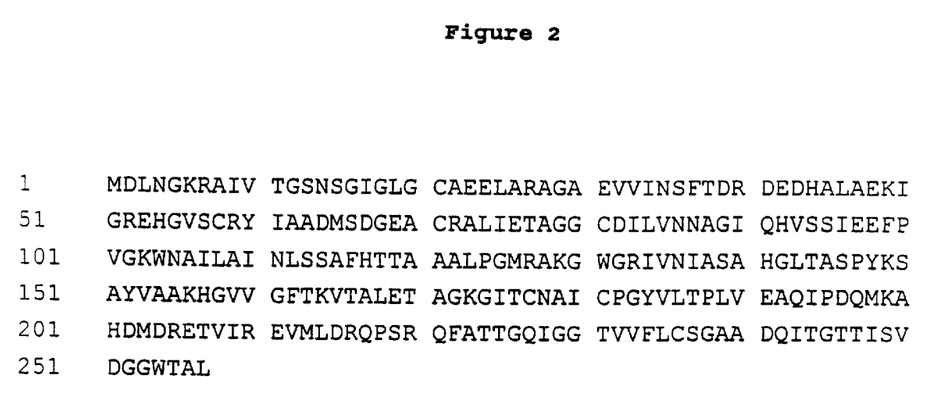
FIG. 2: Amino acid sequence of 3-HBDH from Rhodobacter spec.
Figure 3:
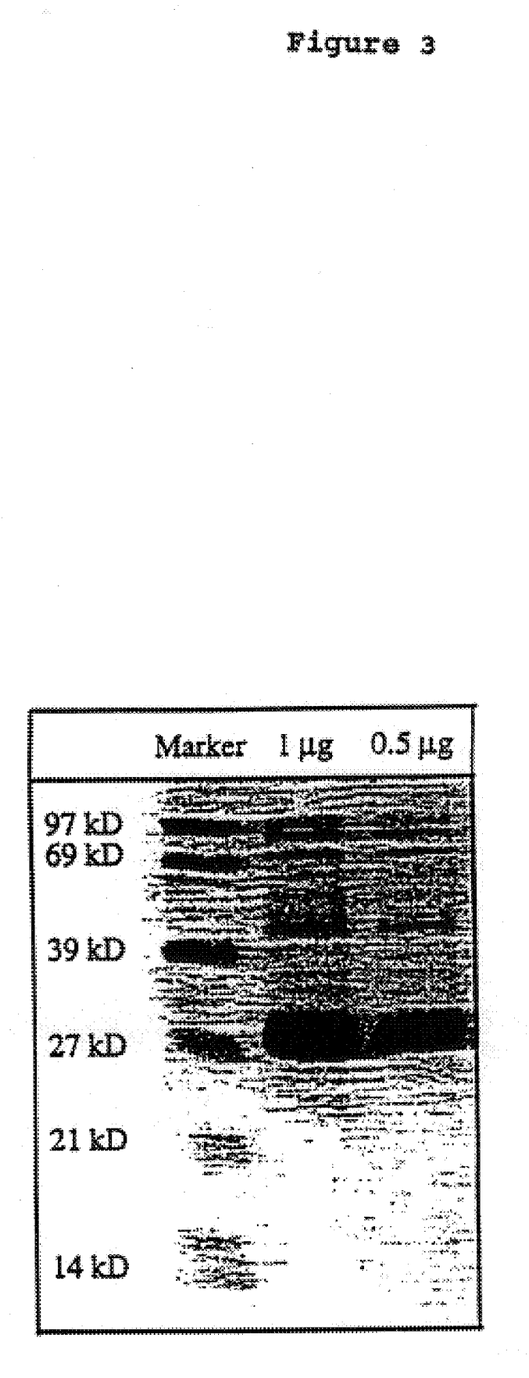
FIG. 3: PSDS-PAGE of a highly concentrated 3-HBDH from Rhodobacter spec. The protein was expressed in *E. coli* and purified by means of phenyl Sepharose chromatography. Samples containing 1 µg and 0.5 µg protein were applied.

A preferred embodiment of the enzyme according to the invention is to express a DNA sequence obtainable from the microorganism Rhodobacter sphaeroides which codes for a 3-HBDH protein in an *E. coli* strain for example in the strain HB101 (ATCC 33694). In this manner it is possible to obtain the recombinant microbial 3-HBDH enzyme from the transformed strain by methods known to a person skilled in the art in a high yield and purity, with a specific activity of at least 200 U/mg protein. The molecular weight of the enzyme according to the invention composed of four subunits is between 24,000 and 30,000 Dalton (SDS-PAGE). Furthermore a preferred embodiment of the enzyme has a temperature optimum of ca. 50° C. a pI of 5.90 as well as a pH optimum of ca. pH 7 to 8.5 (0.2 M potassium phosphate or Tris/HCl buffer) and is characterized by the amino acid sequence shown in SEQ ID NO.2 and FIG. 2.

A further subject matter of the invention is a method for the determination of ketone bodies in the presence of the recombinant microbial enzyme according to the invention. In principle the test can be carried out by known methods i.e. with regard to the other components that are required (e.g. Bergmeyer, H. U. et al. (1967), Biochem. J. vol. 102, 423–431).

In general, the enzymatic test follows the procedure of a routine test except that the protein according to the invention is added to start the reaction, instead of enzymes known in the art. Prior to adding the protein of the invention, a buffer, a coenzyme and a suitable enzyme substrate are mixed and conditioned, preferably in a cuvette at 25° C.

Accordingly, a method for quantitatively determining an amount of a ketone body in a body fluid sample comprises combining the body fluid sample, a buffer solution, and a coenzyme, and thereafter the protein of the invention, reacting the ketone body and the coenzyme to oxidize or reduce an amount of the coenzyme, wherein the reaction is mediated by the protein, optically determining the amount of coenzyme oxidized or reduced, and correlating the amount of coenzyme oxidized or reduced with the amount of the ketone body.

FIGURE LEGENDS

FIG. 1: Nucleotide sequence of 3-HBDH from Rhodobacter spec. (nucleotides 467–1237).

FIG. 4: Kinetic data (absorbance/time) for the formation of acetate and NADH using the inventive enzyme according to example 2;

series 1, series 2 (table 2).

The invention is further elucidated by the following examples:

EXAMPLE 1

Cloning of 3-HBDH

In order to isolate chromosomal DNA, 0.7 g bacterial wet weight (Rhodobacter sphaeroides) was resuspended in 2 ml 50 mM Tris pH 8.0, 1 mM EDTA, 6.7% sucrose and incubated for 15 min at 37° C. Subsequently 50 mg lysozyme was added and it was incubated for a further 10 min at 37° C. 1.25 ml 0.5 M EDTA pH 8.0 was added to inhibit DNAses. The bacteria were lysed for 10 min at 37° C. by adding 0.75 ml 20% SDS, 50 mM Tris pH 8.0, 20 mM EDTA. Subsequently 2 mg proteinase K was added and incubated for 3 hours at 37° C. 5 M sodium perchlorate was added up to a final concentration of 1 M. The solution was then extracted twice with phenol/chloroform/isoamyl alcohol (25:24:1) and twice with chloroform. The chromosomal DNA was precipitated for 30 min at −20° C. with 2.5 volumes 100% ethanol and 1/10 volume 3 M sodium acetate. The pellet was washed with 5 ml 70% ethanol, air dried and resuspended in TE (10 mM Tris/HCl pH 7.8; 1 mM EDTA). In order to digest RNA, the solution was incubated for 2 hours at 37° C. with 100 µg/ml RNaseA.

Alternatively chromosomal DNA can be isolated with the aid of the genomic DNA purification kit sold by the QIAGEN company according to the manufacturer's instructions.

The DNA fragment coding for the N-terminal amino acids 1–163 (SEQ ID NO.2) was amplified by means of PCR using degenerate primers which were derived from the available peptide sequences. The DNA fragment was cloned into a suitable vector e.g. the vector pCRII (Clark, J. M. (1988), Nucl. Acids Res. vol. 16, 9677–9686 and Mead, D. et al. (1991), Bio/Technology vol. 9, 657–663) and sequenced. The TA cloning kit sold by the Invitrogen Company proved to by useful for this.

The 3'-terminal end of the 3-HBDH gene (corresponds to amino acid residues 164–257, SEQ ID NO.2) was isolated by Southern blot analysis and by preparing a partial gene bank. 10 µg aliquots of chromosomal DNA were digested with various restriction enzymes (BamHI, NaeI, SmaI, PstI, NcoI), separated by gel electrophoresis and transferred onto a nylon membrane. A 514 bp Eco-RI fragment which contained the first 489 bp of the 3-HBDH gene served as a probe to detect homologous fragments in the chromosomal DNA. These fragments were labelled by random priming according to Maniatis et al., Molecular cloning, A Laboratory Manual, 2nd Edition, Cold Spring Harbor Laboratory Press (1989) using digoxigenin-dUTP (DIG High Prime DNA Labeling and Detection Starter Kit II, Boehringer Mannheim Co.). DNA restriction fragments which gave a positive signal with the probe were extracted from the gel according to Maniatis et al. (1989), Molecular Cloning, A Laboratory Manual, 2nd. Edition, Cold Spring Harbor Laboratory Press) and ligated into the vector pBluescript II SK+

(Stragene Co.) in order to prepare a partial gene bank and transformed into *E. coli* XL1 Blue.

Positive clones were detected with a probe in the colony lift which contained the 5'-terminal 152 bp of the 3-HBDH gene. The probe was synthesized with the aid of PCR and also labelled with digoxigenin-dUTP by means of random priming.

1% of the clones which contained BamHI restriction fragments had a positive signal with the probe that was used. Two selected BamHI clones were sequenced using various internal primers (SEQ ID NO.1). The amino acid sequence derived from this sequence corresponds to the sequence shown in SEQ ID NO.2.

In order to clone the 3-HBDH gene into the expression vectors pKK177-HB and pKKT5, the 3-HBDH gene was amplified by PCR using Taq polymerase (Boehringer Mannheim Co.). The oligonucleotides that were used also served to simultaneously introduce restriction enzyme cleavage sites (EcoRI at the 5' end and HindIII at the 3' end of the 3-HBDH gene). The PCR cycles were: 3 minutes 95° C. (denaturation); 30 cycles: 2 minutes 95° C. (denaturation), 1 minute 57° C. (annealing), 1 minute 72° C. (polymerization); 7 minutes 72° C. (polymerization). The BamHI clones which yielded a positive signal in the colony lift and that were sequenced were used as a template DNA. The amplified DNA fragment was purified according to Vogelstein, B. and Gillespie, D. (1979), Proc. Natl. Acad. Sci. USA vol. 76, 615–619 for example with the aid of a High Pure PCR purification kit (Boehringer Mannheim Co.), cleaved with the restriction enzymes EcoRI and HindIII and, after separation on a 1% agarose gel, it was eluted from the gel, ligated into the two expression vectors and thus transformed into *E. coli* XL1 Blue. Positive clones were identified by restriction digestion with the same enzymes and sequenced as a control.

Various *E. coli* strains (e.g. RR1 (ATCC 35102), HB101 (ATCC 33694), JM83 (ATCC 35607) were transformed with the recombinant plasmid 3-HBDHxpKKT5 together with the helper plasmid pUBS520.

In order to express the 3-HBDH, overnight cultures of the *E. coli* strains were inoculated 1/60 in Luria broth (containing 100 μg/ml ampicillin and 50 μg/ml kanamycin) and induced at an OD550 of 0.5 with IPTG (isopropylthio-galactoside; 1 mM final concentration). After induction the cultures were incubated for a further 4 hours at 37° C. The cultures were centrifuged, the cell pellet was resuspended in 50 mM potassium phosphate, pH 7.6, 0.1 mM calcium chloride, 0.1 mM magnesium chloride and lysed with the aid of a French press. After filtering the lysate, ammonium sulfate was added to the extract until a conductivity of 150 mS/cm was reached. After adjusting the pH value to 7.6, the filtrate was applied to a phenyl Sepharose column and fractionated with a linear gradient which extended from 1.2 M to 0 M ammonium sulfate. Fractions which contained 3-HBDH activity were dialysed against 0.05 M Tris-HCl, pH 7.8, 1 mM dithiothreitol.

In this manner a protein was obtained with 3-HBDH activity with a purity of ca. 80% and a specific activity of over 200 U/mg to ca. 250 U/mg protein (1 unit of enzyme activity corresponds to the amount of enzyme which catalyses the conversion of 1 μmol substrate per minute). The result of a purification process for the enzyme according to the invention is shown in table 1.

TABLE 1

| Sample/Step | % of resid. activity | MU | SA [U/mg] |
|---|---|---|---|
| initial in the turbid solution | 100 | 12.6 | — |
| after centrifugation including Polymin G20 | 101 | 12.7 | 170 |
| +AS and centrifugation | 100 | 12.6 | 140 |
| phenyl-Sepharose | 84 | 10.6 | 230 |
| after ultrafiltration | 78 | 9.87 | 240 |
| after blending and sterile filtration | 83 | 10.5 | 220 |
| after lyophilization (raffinose) | 62 | 7.81 | >225 |

EXAMPLE 2

The enzymatic test was carried out as follows. A buffer solution (1 ml 0.2 M Tris-HCl, pH 8.0), 0.1 ml NAD$^+$ (20 mg/ml aqueous solution) and 0.25 ml substrate solution (sodium β-hydroxybutyrate, 20 mg/ml aqueous solution) were conditioned at 25° C. (in a cuvette with a 1 cm light path). The reaction was started by adding 0.025 ml of a dilute solution containing the enzyme according to the invention and the reaction rate was monitored by measuring the linear change of absorbance at 340 nm (Table 2).

TABLE 2

| Time [min] | series 1 absorbance at 340 nm | series 2 absorbance at 340 nm |
|---|---|---|
| 0 | 0.1693 | 0.1624 |
| 0.5 | 0.18 | 0.1777 |
| 1 | 0.1927 | 0.1869 |
| 1.5 | 0.2057 | 0.1997 |
| 2 | 0.2249 | 0.2146 |
| 2.5 | 0.2309 | 0.224 |
| 3 | 0.2436 | 0.2376 |
| 3.5 | 0.2561 | 0.2499 |
| 4 | 0.2691 | 0.2623 |
| 4.5 | 0.2827 | 0.2757 |
| 5 | 0.2951 | 0.2883 |
| 5.5 | 0.3077 | 0.3001 |
| 6 | 0.3203 | 0.3134 |
| 6.5 | 0.3333 | 0.326 |
| 7 | 0.3466 | 0.339 |
| 7.5 | 0.3591 | 0.3513 |
| 8 | 0.3717 | 0.3641 |
| 8.5 | 0.3843 | 0.3766 |
| 9 | 0.3973 | 0.3891 |
| 9.5 | 0.4099 | 0.4091 |
| 10 | 0.4227 | 0.4139 |
| rate | 0.0254 | 0.0251 |
| standard deviation | 0.0015 | 0.0009 |
| result | 0.2541 | |

Figure 4:
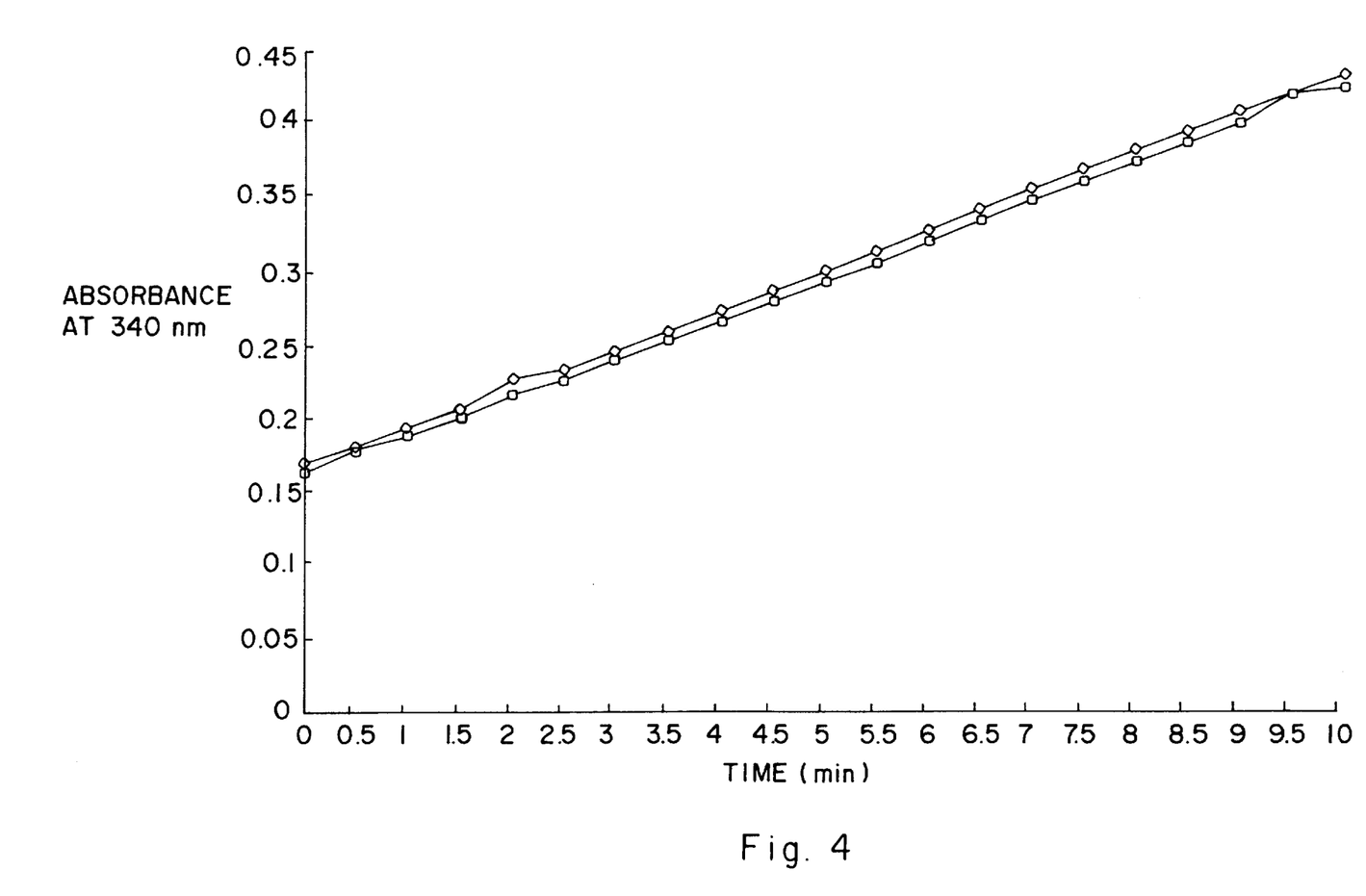

FIG. 4 shows the corresponding graphical evaluation.

We claim:

1. A purified protein having 3-hydroxybutyrate dehydrogenase enzyme activity, wherein the protein has the following physicochemical properties: (1) catalysis of the oxidation of hydroxybutyric acid to acetoacetic acid and conversion of $NAD^+$ to NADH; (2) molecular weight of 24,000 to 30,000 Daltons, as determined by SDS-polyacrylamide gel electrophoresis; (3) optimal pH of about 7 to 8.5; optimal temperature of about 50° C.; and specific activity of at least 200 U/mg protein, and wherein the bacterial protein is obtainable from a bacterial genera selected from the group consisting of Rhodobacter, Rhodospirillum and Pseudomonas.

2. The protein of claim 1, wherein the protein has a pI of about 5.90.

3. The protein of claim 1, wherein the protein is produced by transforming a DNA sequence encoding the protein, operably linked to a promoter, into a heterologous microorganism, expressing the transformed DNA sequence in the microorganism to produce the protein and isolating the protein so produced.

4. The protein of claim 3, wherein the DNA sequence is obtainable from a bacteria of the genus Rhodobacter.

5. The protein of claim 4, wherein the DNA sequence is obtainable from *Rhodobacter sphaeroides*.

6. The protein of claim 1, wherein the protein has the amino acid sequence of SEQ ID NO: 2.

7. The protein of claim 3, wherein the heterologous microorganism is an *E. coli* cell.

* * * * *

SEQUENCE LISTING

<160> NUMBER OF SEQ ID NOS: 2

<210> SEQ ID NO: 1
<211> LENGTH: 1406
<212> TYPE: DNA
<213> ORGANISM: Rhodobacter sphaeroides
<220> FEATURE:
<221> NAME/KEY: CDS
<222> LOCATION: (467)..(1237)

<400> SEQUENCE: 1

```
ccgcccttcg gcgcgtcggg atttgcatat ggcagagaca caaaatccgg tggaagcgcc    60
ggttcgccat acatagctat gccgtgccgg ggttcggcgg ccagcgtcgt gcccagaacg   120
gcaagcccga gagccagcgc ggcgcccctc aggcgggacc ggaattcctg tatcattcgg   180
gcaacagctc ctcggtggcc gatccgcagg gggccagatt tacccgcggg cggtaacctt   240
ttcaaacttt taccttggac agcggcggag aaggtcgtat aagtatccca ctgctcgata   300
ggtttcttgc ctgtatgaaa cctgcctcaa cgacttaacg ccggcttcgc gccggcgttt   360
tttttcgcgc ttcgcgaatg acaggcgccc cggtctccgt gccatctcgc catcccgcgg   420
cccattggct aggtcttggc cagtgcacat gacgggaggc aggatc atg gat ctg       475
                                                   Met Asp Leu
                                                     1
```

```
aac ggc aag cgg gca atc gtc acc ggc tcg aac tcg ggc atc ggg ctg     523
Asn Gly Lys Arg Ala Ile Val Thr Gly Ser Asn Ser Gly Ile Gly Leu
        5                  10                  15 ggc tgc gcc gaa gag ctg gcg cgc gcc ggc gcc gag gtt gtc atc aac     571
Gly Cys Ala Glu Glu Leu Ala Arg Ala Gly Ala Glu Val Val Ile Asn
 20                  25                  30                  35 tcc ttc acc gac cgc gac gag gat cac gcg ctg gcc gag aag atc ggc     619
Ser Phe Thr Asp Arg Asp Glu Asp His Ala Leu Ala Glu Lys Ile Gly
                 40                  45                  50 cgc gaa cat ggc gtg agc tgc cgc tac atc gcg gcc gac atg tcg gac     667
Arg Glu His Gly Val Ser Cys Arg Tyr Ile Ala Ala Asp Met Ser Asp
             55                  60                  65 ggc gaa gcg tgc cgg gcg ctg atc gag acg gcg ggc ggc tgc gac atc     715
Gly Glu Ala Cys Arg Ala Leu Ile Glu Thr Ala Gly Gly Cys Asp Ile
         70                  75                  80 ctc gtg aac aac gcg ggc atc cag cat gtc tcg tcg atc gag gag ttc     763
Leu Val Asn Asn Ala Gly Ile Gln His Val Ser Ser Ile Glu Glu Phe
     85                  90                  95 ccg gtc ggg aag tgg aac gcg atc ctc gcg atc aac ctc tcg tcg gcc     811
Pro Val Gly Lys Trp Asn Ala Ile Leu Ala Ile Asn Leu Ser Ser Ala
100                 105                 110                 115 ttc cac acc acg gcg gcg gcg ctg ccg ggg atg cgg gcg aag ggc tgg     859
Phe His Thr Thr Ala Ala Ala Leu Pro Gly Met Arg Ala Lys Gly Trp
                120                 125                 130 ggg cgg atc gtc aac atc gcc tcg gcg cac ggg ctg acg gcg agc ccc     907
Gly Arg Ile Val Asn Ile Ala Ser Ala His Gly Leu Thr Ala Ser Pro
            135                 140                 145 tac aag tcg gcc tat gtc gcg gcc aag cac ggg gtg gtg ggc ttc acc     955
Tyr Lys Ser Ala Tyr Val Ala Ala Lys His Gly Val Val Gly Phe Thr
        150                 155                 160 aag gtc acc gcg ctc gag acc gcg ggc aag ggc atc acc tgc aac gcg    1003
Lys Val Thr Ala Leu Glu Thr Ala Gly Lys Gly Ile Thr Cys Asn Ala
165                 170                 175 atc tgc ccg ggc tat gtg ctg acg ccg ctg gtc gag gcg cag atc ccc    1051
Ile Cys Pro Gly Tyr Val Leu Thr Pro Leu Val Glu Ala Gln Ile Pro
```

-continued

```
                180                 185                 190                 195
gac cag atg aag gcg cac gac atg gac cgc gag acg gtg atc cgc gag         1099
Asp Gln Met Lys Ala His Asp Met Asp Arg Glu Thr Val Ile Arg Glu
            200                 205                 210 gtg atg ctc gac cgc cag ccc tcg cgc cag ttc gca acg acc ggt cag         1147
Val Met Leu Asp Arg Gln Pro Ser Arg Gln Phe Ala Thr Thr Gly Gln
        215                 220                 225 atc ggc ggc acg gtg gtg ttc ctc tgc tcg ggt gcg gcc gat cag atc         1195
Ile Gly Gly Thr Val Val Phe Leu Cys Ser Gly Ala Ala Asp Gln Ile
        230                 235                 240 acc ggg acg acg atc tcg gtg gat ggg ggc tgg acc gcc ctc                 1237
Thr Gly Thr Thr Ile Ser Val Asp Gly Gly Trp Thr Ala Leu
    245                 250                 255 tgacgggcgg tccttcggca actcccgggt cagcctctgg cgatggcgcg ggcgatgtcg       1297
gtcgcgagcc gggcgttcga caggacgagc gcccggttgg cctcgagcga ccggccctcg       1357
gtcagatcga agatcaggtc gagcaggaac ggcgtcacgg ccttggcgg                   1406
```

<210> SEQ ID NO: 2
<211> LENGTH: 257
<212> TYPE: PRT
<213> ORGANISM: Rhodobacter sphaeroides

<400> SEQUENCE: 2

```
Met Asp Leu Asn Gly Lys Arg Ala Ile Val Thr Gly Ser Asn Ser Gly
  1               5                  10                  15

Ile Gly Leu Gly Cys Ala Glu Leu Ala Arg Ala Gly Ala Glu Val
             20                  25                  30

Val Ile Asn Ser Phe Thr Asp Arg Asp Glu Asp His Ala Leu Ala Glu
         35                  40                  45

Lys Ile Gly Arg Glu His Gly Val Ser Cys Arg Tyr Ile Ala Ala Asp
     50                  55                  60

Met Ser Asp Gly Glu Ala Cys Arg Ala Leu Ile Glu Thr Ala Gly Gly
 65                  70                  75                  80

Cys Asp Ile Leu Val Asn Asn Ala Gly Ile Gln His Val Ser Ser Ile
                 85                  90                  95

Glu Glu Phe Pro Val Gly Lys Trp Asn Ala Ile Leu Ala Ile Asn Leu
            100                 105                 110

Ser Ser Ala Phe His Thr Thr Ala Ala Leu Pro Gly Met Arg Ala
        115                 120                 125

Lys Gly Trp Gly Arg Ile Val Asn Ile Ala Ser Ala His Gly Leu Thr
    130                 135                 140

Ala Ser Pro Tyr Lys Ser Ala Tyr Val Ala Ala Lys His Gly Val Val
145                 150                 155                 160

Gly Phe Thr Lys Val Thr Ala Leu Glu Thr Ala Gly Lys Gly Ile Thr
                165                 170                 175

Cys Asn Ala Ile Cys Pro Gly Tyr Val Leu Thr Pro Leu Val Glu Ala
            180                 185                 190

Gln Ile Pro Asp Gln Met Lys Ala His Asp Met Asp Arg Glu Thr Val
        195                 200                 205

Ile Arg Glu Val Met Leu Asp Arg Gln Pro Ser Arg Gln Phe Ala Thr
    210                 215                 220

Thr Gly Gln Ile Gly Gly Thr Val Val Phe Leu Cys Ser Gly Ala Ala
```

```
                    -continued
225             230             235             240

Asp Gln Ile Thr Gly Thr Thr Ile Ser Val Asp Gly Gly Trp Thr Ala
                245             250             255
Leu
```